(12) United States Patent
Giori (10) Patent No.: US 8,388,881 B2
(45) Date of Patent: Mar. 5, 2013

(54) METHOD FORMING A ONE-PIECE ARTICULATING SPACING DEVICE FOR A KNEE JOINT

(75) Inventor: Nicholas John Giori, Palo Alto, CA (US)

(73) Assignees: The Board of Trustees of the Leland Stanford Junior University, Palo Alto, CA (US); The United States of America, as represented by the Department of Veterans Affairs, Washington, DC (US)

( * ) Notice: Subject to any disclaimer, the term of this patent is extended or adjusted under 35 U.S.C. 154(b) by 52 days.

(21) Appl. No.: 12/781,517

(22) Filed: May 17, 2010

(65) Prior Publication Data

US 2010/0292803 A1    Nov. 18, 2010

Related U.S. Application Data

(60) Provisional application No. 61/178,974, filed on May 17, 2009.

(51) Int. Cl.
*B29C 39/10* (2006.01)
(52) U.S. Cl. .................. 264/250; 264/255; 264/279
(58) Field of Classification Search .................. None
See application file for complete search history.

(56) References Cited

U.S. PATENT DOCUMENTS

| | | | | |
|---|---|---|---|---|
| 2004/0236429 A1* | 11/2004 | Ensign et al. | ............. | 623/20.32 |
| 2008/0097606 A1* | 4/2008 | Cragg et al. | ............. | 623/14.12 |
| 2011/0172768 A1* | 7/2011 | Cragg et al. | ............. | 623/14.12 |

\* cited by examiner

*Primary Examiner* — Edmund H. Lee
(74) *Attorney, Agent, or Firm* — Andrea Blecken

(57) ABSTRACT

The present invention provides molds and methods for producing articulating spacers that are custom-fit to the bone and can be used in two-stage revision knee arthroplasty and other orthopaedic surgery.

4 Claims, 12 Drawing Sheets

METHOD FORMING A ONE-PIECE ARTICULATING SPACING DEVICE FOR A KNEE JOINT

RELATED APPLICATION

This application claims priority and other benefits from U.S. Provisional Patent Application Ser. No. 61/178,974, filed May 17, 2009, entitled "Mold and method of forming an articulating spacing device for a joint". Its entire content is specifically incorporated herein by reference.

STATEMENT OF GOVERNMENTAL SUPPORT

This invention was made with support of the U.S. Government represented by the Department of Veterans Affairs. The Government has certain rights in this invention.

TECHNICAL FIELD OF THE INVENTION

The present invention relates to the field of implants for use in orthopedic surgery, in particular, for use in creating a temporary articulating spacer in two-stage reimplantation total knee arthroplasty.

BACKGROUND

Figure 1:
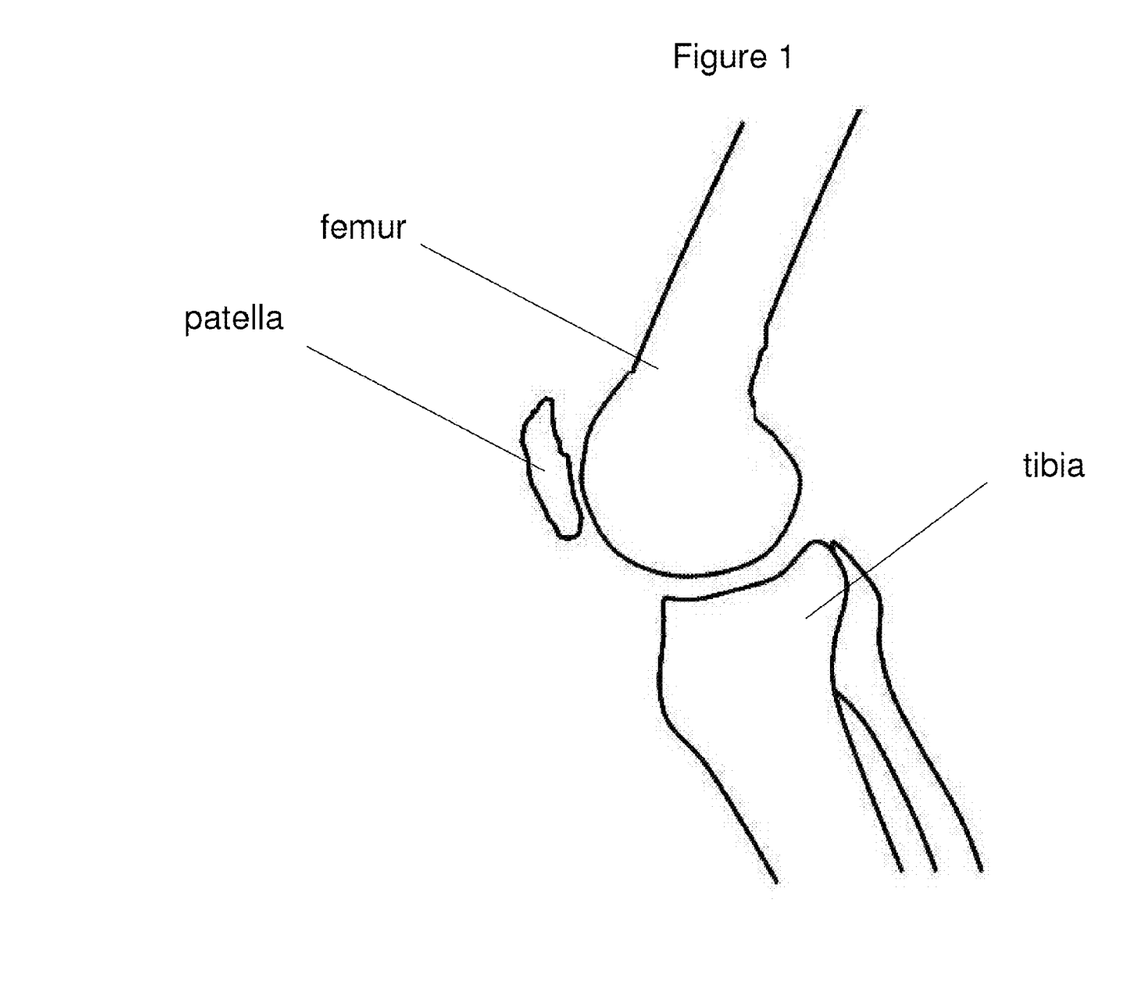
FIG. 1 shows a lateral view of a knee.

The anatomy of the knee is primarily composed of two major bones, the tibia and the femur (see FIG. 1). These two bones meet to form a joint between the proximal tibia and the distal femur. A third member of the joint is the patella, or the kneecap. The knee joint is cushioned by articular cartilage that covers the ends of the tibia and femur, as well as the underside of the patella. The lateral meniscus and medial meniscus are pads of cartilage that further cushion the joint, acting as shock absorbers between the bones.

A healthy knee joint is able to withstand great forces that are exerted as the knee flexes and extends and supports the weight of the body. However, when the knee joint degenerates and becomes arthritic due to an injury or infection of the joint or due to aging, it may become necessary to reconstruct or replace the knee joint. When a total knee replacement (arthroplasty) is required, the natural knee joint is replaced with a prosthetic knee joint. A certain percentage of patients who undergo a total knee replacement surgery eventually contract an infection in the knee joint at the surgical site necessitating further surgery for control of the infection.

Figure 2:
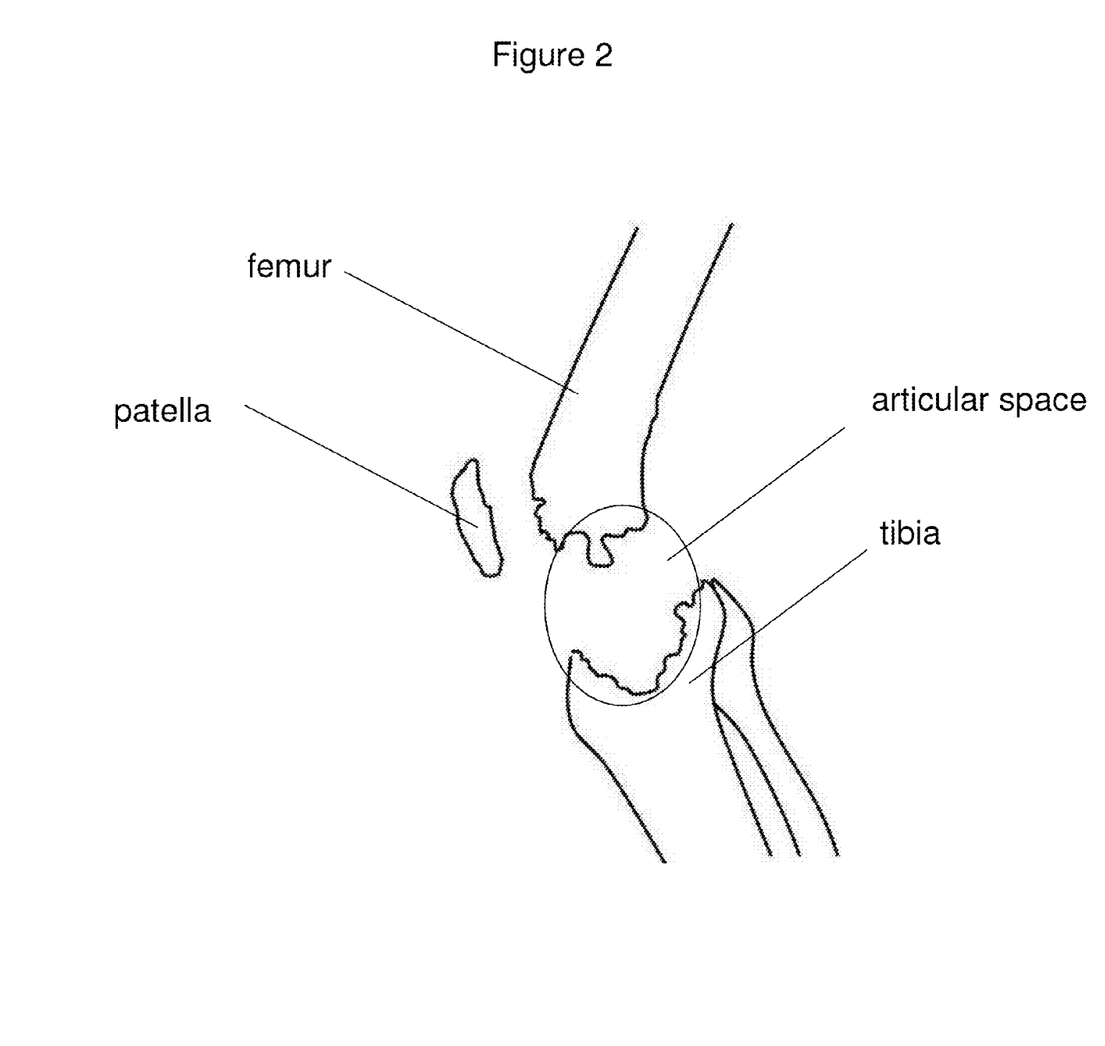
FIG. 2 shows a lateral diagram of a knee with destruction of the joint surface and view of the articular space.

Two stage reimplantation total knee arthroplasty has become an increasingly common operation for the treatment of infected total knee arthroplasty. The treatment of infected total knee arthroplasty requires the removal of the old prosthesis (artificial joint) and placement of a spacing device to treat the infection before a new prosthesis is implanted. The spacing device is needed, since it is important to maintain the original space between the joints in order to prevent a reduction in the articular space (see FIG. 2), retraction of the tissues, atrophy of the joints and loss of muscular elasticity as well as tone. In addition, the spacing device contains antibiotics that elute from the spacer after implantation, locally delivering antibiotics to the site of the infection. This is an essential part of the overall treatment to eradicate the infection.

Non-articulating as well as articulating spacing devices are known in the art for artificial knee, hip and shoulder joints. Traditional non-articulating, fixed spacing devices for the knee are applied as a bone cement block that is mixed with antibiotics by the surgeon and is placed between the tibia and the femur. Though these fixed spacing devices have been shown to be effective in treating infections and maintaining space for reimplantation of a second knee replacement after the infection has been eradicated, these spacers do not allow for knee movement. As treatment for infection after knee replacement can take many months, it is very inconvenient for the patient to not be able to move his knee for such an extended period of time.

Prefabricated and preformed articulating spacing devices made of bone cement and other materials exist that allow the patient limited mobility (e.g. Interspace® knee spacer from Exactech, Gainesville, Fla.), but, as with limited size options, do not provide an optimal fit to the particular bony anatomy of each patient. In addition, preformed articulating spacing devices do not give the surgeon the flexibility to select the type and concentration of antibiotic in the spacer. Since different bacteria have different sensitivities to different antibiotics, this is a significant disadvantage.

Other existing technologies (e.g. Stage One molds, Biomet Inc.) involve the surgeon using two preformed molds to make articulating spacers. With these technologies, the surgeon can select the type and concentration of antibiotic in the cement, but the molding process occurs outside of the patient in two separate molds, one mold to create the femoral spacer component, and the other to create the tibial spacer component. The surgeon must then wait for the cement to harden, remove the spacer from each mold, and then either place these two molded articulating spacer components in the patient, and not achieve a custom fit with the irregular bone surface of the patient, or the surgeon must then mix a second batch of cement to cement these spacers on the patients bone. Though this solution provides the surgeon with the capability of selecting the type and concentration of antibiotic in the spacer, the only way to achieve a custom fit with the irregular bone surface of each patient is to mix two batches of cement, one to make the molded components and the other to apply them to the existing irregular bone surfaces of the patient, a process that takes considerable valuable operating room time.

Another proposed solution to this problem involves placing sterile metal and plastic knee replacement components in the knee with cement that has been mixed with antibiotics. This solution is controversial as it involves placing a large quantity of inert material (metal and plastic) that does not elute antibiotics into the infected site.

Reproducing the knee joint using custom-fit temporary spacing devices that have only antibiotic eluting material and that simulate the natural shape of the tibial and femoral components of the knee joint would be superior to the fixed spacing devices, since they provide an optimal fit to the particular bony anatomy of a patient, permit movement of the leg, and can still deliver antibiotics to aid in the treatment of infection and maintaining space for future surgery. There is a clear need in the art for custom-fit articulating spacers that provide the surgeon with the ability to deliver a specific antibiotic at a specific concentration, that only require one round of mixing cement, and that do not require post-molding modification.

The present invention fully addresses this need.

SUMMARY

The present invention provides compositions and methods for forming and clinically utilizing articulating spacing devices. In a particular embodiment of the present invention, an articulating spacing device for two stage knee arthroplasty is described which uses molds that are shaped like a very thin femoral component of a total knee replacement and that are available in different sizes to fit the size of each patient.

Those having ordinary skill in the relevant art will appreciate the advantages provided by the features of the present invention. For example, it is a feature of the present invention to provide custom-sized molds for the knee joint that are formed in situ during surgery which are practical, time-efficient and inexpensive to manufacture, as well as adaptable to various bony anatomy. A particularly noteworthy and advantageous feature of the present invention which has not been a feature of other molds previously described for creating an articulating cement spacer is that one single mold simultaneously molds the cement on both sides of the joint (the distal femur and the proximal tibia), and does this in situ (in the patient) requiring only one mixing of cement. Further objectives of the present invention are to provide a method of forming a temporary spacing implant that simulates the biomechanics of the joint, for example the natural knee joint, such that a patient may have mobility and range of motion in the knee joint during the time of implantation and before the revision surgery.

The above summary is not intended to include all features and aspects of the present invention nor does it imply that the invention must include all features and aspects discussed in this summary.

INCORPORATION BY REFERENCE

All patent and non-patent publications mentioned in this specification are herein incorporated by reference to the same extent as if each individual publication or patent application was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

DEFINITIONS

The practice of the present invention may employ conventional techniques in total knee and revision arthroplasty, which are within the capabilities of a person of ordinary skill in the art to which the present invention belongs. Such techniques are fully explained in the literature. For definitions, terms of art and standard methods known in the art, see, for example, Scuderi and Tria "Knee Arthroplasty Handbook: Techniques in total knee and revision arthroplasty", Springer 2006, which is in its entirety herein incorporated by reference.

Unless defined otherwise, all technical and scientific terms used herein have the same meaning as commonly understood by a person of ordinary skill in the art to which the present invention belongs. The following definitions are intended to also include their various grammatical forms, where applicable.

The terms "spacing device" and "spacer" are used interchangeably.

The terms "temporary spacing device", "temporary spacing implant", "custom-fit spacing device", "custom-fit spacing implant" are used interchangeably.

DETAILED DESCRIPTION

The present invention provides compositions and methods for forming and clinically utilizing articulating spacing devices; such methods are carried out in the course of the surgery and, therefore, require minimal additional time. In a particular embodiment of the present invention, an articulating spacing device for two stage knee arthroplasty is described which is formed using molds that are shaped like a thin femoral component of a total knee replacement. The molds can be supplied in an array of sizes to meet various individuals' needs and to accommodate all the potential possibilities in anatomical differences of individuals; for example, the molds can be supplied in five different mold sizes (extra small, small, medium, large, extra large). More or less than five mold sizes may be used by the present invention, dependent upon the desired range of bones to be fitted by the molds.

In certain embodiments, the molds to form a temporary spacing implant are shaped like a femoral component of a total knee replacement. In other embodiments, the molds to form a temporary spacing implant include a convex and a concave side, where the concave side of the mold forms one side of the newly formed joint surface and the convex side of the mold forms the other side of the joint surface.

In certain embodiments, the molds to form a temporary spacing implant are made out of sheet-metal. In other embodiments, the molds to form a temporary spacing implant are made out of an alternative metal, metal alloy or a rigid plastic or out of an elastic material such as silicone.

In certain embodiments, the molds to form a temporary spacing implant are used to create an implant out of bone cement that can be mixed with a standard antibiotic in a typical concentration, as known in the art of orthopedic surgery. In other embodiments, the molds to form a temporary spacing implant are used to create an implant out of a biocompatible material other than bone cement; such biocompatible material may be presently known or may become known in the future in the art to form such implants and can be a synthetic material or a material originating from tissue engineered cells. Therefore, it is contemplated that a myriad of other materials that are also biocompatibly suitable for surgical use may be utilized as the implant material without departing from the scope of the present invention.

Advantageously, embodiments of the spacing devices of the present invention allow for custom molding to fit the particular bony anatomy of each individual patient and allow mobility and flexion of the concerned joint.

Arthroplasty

Arthroplasty is a surgical procedure to reconstruct and/or realign a joint that has become dysfunctional due to injury or aging with the objectives to minimize joint pain, to stabilize the joint and to restore range of motion as best as possible. Osteoarthritis, a degenerative joint disease, is the most common condition causing joint dysfunction and even joint destruction followed by severe pain and impaired joint movement due to joint stiffness.

Each joint has, in a healthy condition, a specific range of motion which is expressed in degrees and which indicates the direction and distance a joint can maximally move.

Joint resection and interposition to create a new articulating surface is known as arthroplasty surgery and is common in the hip, knee, shoulder, ankle, elbow, and finger joint. Isolated joint resection (resection arthroplasty) results in an increased space between the articulating bones, usually improving the range of motion and decreasing pain. Resection arthroplasty, however, does not recreate a stable articulating joint, resulting in weakness and instability. Reconstructing the joint surface with interposed material such as a prosthesis can achieve pain relief, improve range of motion, and provide a stable and strong joint. Such a prosthesis can be synthetic and be made of plastic, metal, ceramic or can be formed from body tissue such as skin, muscle or fascia.

In recent years, total joint replacement or total joint arthroplasty with artificial joints (prostheses) has become a feasible and often preferred choice of treatment for advanced arthritis of the hip and knee. Since currently available artificial joints (in particular, artificial knee and hip joints) may have a limited life span, and repeated joint replacement is not always possible, prosthetic joint replacement must be used with caution in the younger and more active patient.

Surgical Intervention at the Knee: Total Knee Arthroplasty

Several procedures are available to correct joint dysfunction ranging from corrective surgeries to total knee replacement. Total knee arthroplasty has become a reliable and reproducible procedure for pain relief and restoration of function in knees with advanced arthritis of the knee (Hofmann et al., 2005). Unfortunately, approximately 1% to 2% of total knee arthroplasties will get infected. Debridement and retention of knee replacement components can be successful in treating acute, early infections, but has not been very successful in treating deep, chronic infections. In the latter case, the infected implants must be removed. Reimplantation can be carried out in one (single) stage (single-stage exchange arthroplasty) or in two stages (Whiteside L A, 1994; Wilde & Ruth, 1988). Two-stage reimplantation for infected knee replacement has been demonstrated to be consistently more effective than single-stage reimplantation and is the current standard technique.

The standard treatment for two-stage reimplantation (revision) total knee arthroplasty is to remove the implanted components, place some sort of an antibiotic impregnated cement spacer to deliver antibiotics locally and maintain space for eventual knee replacement reimplantation, and then treat with antibiotics for a minimum of six weeks to eradicate the infection. Once the infection is proven to be eradicated, a new total knee arthroplasty can be implanted.

Two-stage reimplantation (revision) total knee arthroplasty includes the following procedures. As a first step, the previously implanted prosthesis is surgically removed and the site debrided and thoroughly cleansed. Before a new, permanent prosthesis can be placed in the old surgical site, the infection has to be cleared, which usually can take from six weeks to four months. Therefore, it is common for surgeons to replace the old prosthetic knee with a temporary implant during the time when the infection is cleared up and before the new prosthesis is surgically implanted. The temporary implant is a spacing device, which is typically impregnated with an antibiotic as part of the therapy to rid the surgical site of the infection and which can be made of various materials that do or do not contain bone cement (Whiteside La., 1994).

Utility of the Present Invention

Reproducing the knee joint using temporary spacing implants that simulate the natural tibial and femoral components of the knee joint is desirable because it permits the patient to move his/her leg through a range of motion. Before a new, permanent prosthesis can be placed in the old surgical site, any infection has to be eradicated be treating with antibiotics, which can take from six weeks to four months or longer ('treatment period'). A patient's comfort and emotional well-being during this 'treatment period' is clearly affected by the patient's range of motion. Accordingly, any increase in the range of motion, by allowing the patient to bend his/her knee for sitting in a chair or for riding in a car, will directly increase the patient's comfort and emotional well-being during the 'treatment period'.

Complete immobilization of the knee in an extended position for the entire course of the treatment period can make revision surgery more difficult due to the immobility of the tissues. Prefabricated spacing devices made of cement and other biocompatible materials exist (e.g. Interspace® knee spacer from Exactech, Gainesville, Fla.), but—in contrast to the herein described custom-fit spacers as certain embodiments of the present invention—do not provide an optimal fit to the particular bony anatomy of each patient. A poorly fitting cement spacer can move excessively in relation to the bone it is applied to, and this movement can be painful. Additionally, the prefabricated spacers are supplied with a certain antibiotic at a certain concentration. This may not be optimum for treatment of the infection.

The mold and technique of the present invention allow for custom fabrication of the cement spacer with type and concentration of antibiotics specific for the infection being treated, and for a custom fit to the existing bone surfaces. This minimizes any relative movement against the bone and, therefore, minimizes pain, while allowing for range of motion of the joint. The time required to make the spacing device with the mold and technique of this invention is minimized as only one cement mixing is needed.

In contrast to spacing devices that are in their entirety manually made by the surgeon carrying out the implantation of that device at the time of the surgical operation, the present methodology enables the surgeon to provide the proper, anatomically correct spacing for optimal healing and range of motion. Furthermore, unlike fully manual procedures, the present methodology requires minimal additional time by the surgeon, since it is made with the assistance of a mold, is molded in the wound, molds the femoral and tibial components of the spacer at the same time, requires only one mixing of cement, and does not require any modification of the spacer once the cement has hardened.

While an articulating spacing device for use in two-stage total knee arthroplasty is a preferred embodiment of the present invention, embodiments of the present invention are also envisioned and suitable for use in shoulder joint, elbow joint, ankle joint, wrist joint and hip joint reconstruction.

With respect to joint movement and degrees of movement, the knee is approximately a uniaxial joint with flexion and extension occurring around a single axis and movement in one plane; it enables extension (straightening) and flexion (bending) of the lower leg. The ankle, elbow and finger joints are similar uniaxial joints and a spacer mold for these joints would be similar in design. The shoulder, wrist and hip joints are multiaxial joints with three degrees of freedom and movement in three planes. A spacer mold can be fashioned for these joints, but it would have a hemispherical shape rather than a cylindrical shape in order to allow this multiaxial movement.

In conclusion, articulating spacing devices of the present invention utilize elements in several sizes (molds made out of a rigid or elastic material). The surgeon selects the proper sized mold for the patient and uses this single mold to produce both members of the articulating spacer by simultaneously molding both sides of the joint while the cement hardens in situ. In case of total knee arthroplasty, articulating spacing devices of the present invention simulate the natural shape of the femoral and tibial components of the knee joint.

All members are made out of biocompatible material.

Exemplary Procedure for Creating an Articulating Spacing Device for the Knee

Figure 6:
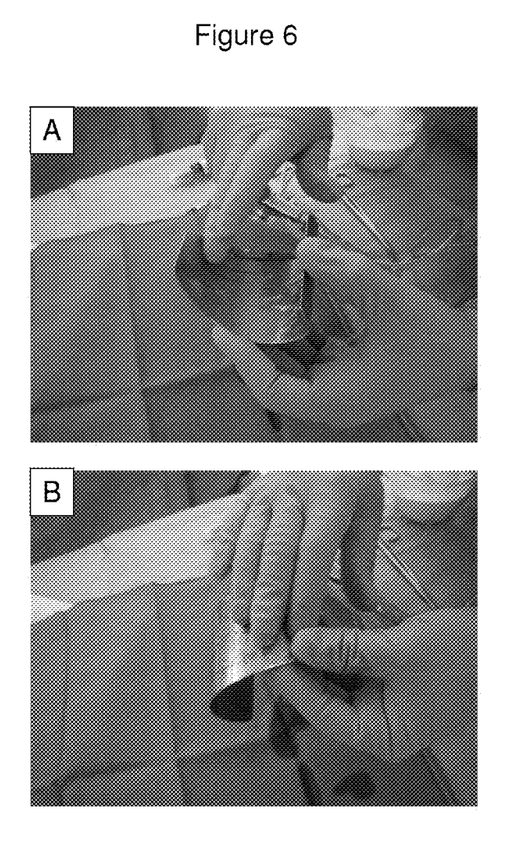
FIG. 6 shows, in accordance with an embodiment of the present invention, a mold made out of stainless sheet metal where a lubricant such as mineral oil is applied to both its concave (PanelA) and convex sides (PanelB), to facilitate easy detachment from the cement to be molded.

In practice, a mold, as exemplified in FIG. 6, Panels A and B, may be used in situ by the surgeon in the following manner. First, bone cement or another biocompatible material known in the art for the fabrication of temporary implants, is mixed together with an antibiotic (or a suitable mixture of antibiotics, meaning a mixture of antibiotics which do not adversely interact, are effective against the bacterial infection being treated, and, in the total dosage, do not exceed the safe, therapeutic window) and pressed into the cavity of the mold (see FIG. 7). Cement is then applied within the concave surface of the mold and the mold is then, in accordance with an embodiment of the present invention, applied to the distal end of the femur. Additionally, directly before or after application of the mold to the distal end of the femur, more still pliable bone cement (or other biocompatible material known in the art) is applied to the tibial surface. Both the femoral and tibial cement then harden simultaneously, with the mold acting to form both sides of the articulation simultaneously while the knee is held in proper alignment and in an extended position. Once the cement (or other biocompatible material known in the art) has completely cured and hardened, the surgeon may remove the mold by pulling the mold off of the femur. The removal process acts as the last step in forming both the femoral and tibial components of the temporary spacing implant. It is noted that the removal of the mold may be accomplished by a variety of methods utilizing a variety of devices, each of which are intended to fall within the scope of the present invention.

In accordance with the features described above, a useful method for forming an articulating spacing device for a patient's knee joint includes the steps of:

(a) providing a rigid or elastic mold made out of metal such as sheet-metal, metal alloy, metalloid such as silicon, ceramics, natural or synthetic polymers, said mold being available in many different sizes to accommodate all the potential possibilities in anatomical differences of patients and said mold shaped preferably like a thin femoral component of a total knee replacement;

(b) providing a biocompatible material such as bone cement, mixed with a standard amount of antibiotics as commonly known and used in the art, and substantially filling the cavity of the mold with said biocompatible material to a desired thickness;

(c) positioning the mold on the distal end of the femur;

(d) adding additional biocompatible material to the tibial surface;

(e) extending the knee and holding the leg in proper alignment, allowing the mold to form both the tibial and femoral surfaces as the molding mixture totally hardens;

(f) removing the mold from the femur.

Steps (c) and (d) can be reversed, yielding an identical outcome.

Materials Suitable for Rigid Molds

The molds of the present invention can be provided in a rigid form and be made out of a thin sheet of metal such as stainless steel, platinum, titanium, iridium, an metal alloy such as ferroalloys, alloys of titanium, iridium, platinum or aluminum, a metalloid such as silicon, a non-metal such as ceramic or synthetic polymeric materials such as hard plastic.

Materials Suitable for Elastic Molds

The molds of the present invention can be provided in an elastic form and be made out of a natural elastomer such as rubber or a synthetic elastomer such as ethylene propylene polymers.

Biocompatible Materials (Including Bone Cement)

Materials for implantation must be biocompatible, i.e., it must not elicit an immune response, once implanted into a patient. Optionally, a biocompatible material is able to integrate with the tissue into which it is implanted.

Biocompatible materials that are considered in the context of embodiments of the present inventions include, but are not limited to the different kinds of currently commercially available polymethyl methacrylate-based bone cements. Polymethyl methylacrylate (PMMA) is a synthetic polymer of methyl methacrylate and is produced by polymerization of powdered pre-polymerized polymethyl methacrylate and liquid monomethy methacrylate monomers.

Antibiotics Suitable for Release from Biocompatible Materials Used in an Articulating Spacing Device Antibiotic-loaded bone cement is an effective and proven method for locally delivering antibiotics. Low-dose antibiotic-loaded bone cements (<0.9 g of powdered antibiotic per 10 grams of bone cement) were first approved by the FDA in 2003 for second-stage reimplantation after infected arthroplasties. Nowadays, commonly used concentrations of antibiotic-loaded bone cements range from 0.9-2 g (or higher) of powdered or liquid antibiotic per 10 g of bone cement, depending on the intended purpose, which might be prophylactic to protect against an infection or aggressive in case of the treatment of a high-risk joint that is infected with a possibly drug-resistant organism.

Antibiotics that are commonly used in arthroplasty procedures include, but are not limited to, aminoglycoside antibiotics such as tobramycin sulfate or gentamicin sulfate (a typical concentration is 0.9 g of powdered or liquid tobramycin base or gentamicin base preparation per 10 grams of bone cement) or glycopeptide antibiotics such as vancomycin (a typical concentration is 3 g of powdered or liquid vancomycin per 40 grams of bone cement). The antibiotic cement mixture can be produced manually by handmixing the appropriate amount of powdered antibiotic with the appropriate amount of bone cement or can be a premixed, commercially available formulation. Examples of commercially available antibiotic-loaded bone cements include Simplex™ P with tobramycin sulfate, Palacos® R with gentamicin, SmartSet GMV with gentamicin or DePuy CMW bone cement mixed with vancomycin or gentamicin.

Complete Healing Parameters in Two-Stage Arthroplasty

Successful two stage reimplantation total joint arthroplasty involves removal of the original infected joint replacement and cement, thorough debridement of surrounding tissues, and placement of an antibiotic-eluting cement spacer. Antibiotics are also delivered intravenously for an extended period of time, usually on the order of six weeks. Following this period of antibiotic administration, the patient is typically taken off of antibiotics and monitored to ensure that the infection has been eradicated, as indicated by standard laboratory values including, but not limited to peripheral white blood cell count, erythrocyte sedimentation rate, and C-reactive protein. Abnormally high levels of peripheral white blood cells or abnormally high levels of C-reactive protein indicate an inflammation and likely(continued) infection. An abnormally high erythrocyte sedimentation rate is another indicator of inflammation and likely (continued) infection.

The joint itself can also be aspirated for cell count and culture to rule out persistent infection. Once infection has been determined to be eradicated, a second operation is performed to remove the existing cement spacer and then reimplant a new total joint arthroplasty prosthesis.

Although any methods and materials similar or equivalent to those described herein can also be used in the practice or testing of the present invention, representative illustrative methods and materials are herein described. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Experimental Procedures

The following methods and materials were used in the examples that are described below.

Materials

Implants consisted of DePuy CMW bone cement mixed with vancomycin (3.0 grams per 40 gram package of bone cement).

Surgical Preparation

The patient was brought to the operating room and anesthesized. The operative leg was prepped and draped in the usual sterile fashion. The infected knee was exposed per the surgeon's preferred method and the infected knee replacement components were removed. The knee was thoroughly debrided of retained cement (and/or any other biocompatible material used for the components) and infected tissue and the knee then irrigated copiously. At this point, the surgeon was getting ready to carry out the procedure for creating a custom-fit spacing device (see examples for more detail).

Clinical Evaluation

Postoperatively, a sterile dressing was applied and a drain was placed to suction. X-rays were obtained in the recovery room. The drain was removed at approximately 3 days postoperatively. Depending on the quality of the soft tissues and the type of surgical exposure employed at the time of surgery, range of motion was started on the first postoperative day with physical therapy. Weight bearing was restricted to 50% of body weight. The patient was prepared for outpatient venous administration of antibiotics, and the patient was discharged when ready. At two weeks post surgery, the patient returned for clinical evaluation and wound check. Sutures or staples were removed from the skin and range of motion of the knee was checked. The patient was encouraged to achieve and maintain as much motion as tolerable. Subsequent office visits were directed towards ensuring good wound healing and following the progress of the treatment for infection. Full weight bearing was allowed once the wound had fully healed. Reimplantation of the total knee arthroplasty was done when infection had been eradicated and soft tissues were amenable to surgery. This can take from 6 weeks to 4 months or more.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

General Working Protocol for Creating an Articulating Spacing Device

General Working Protocol

Figure 3:
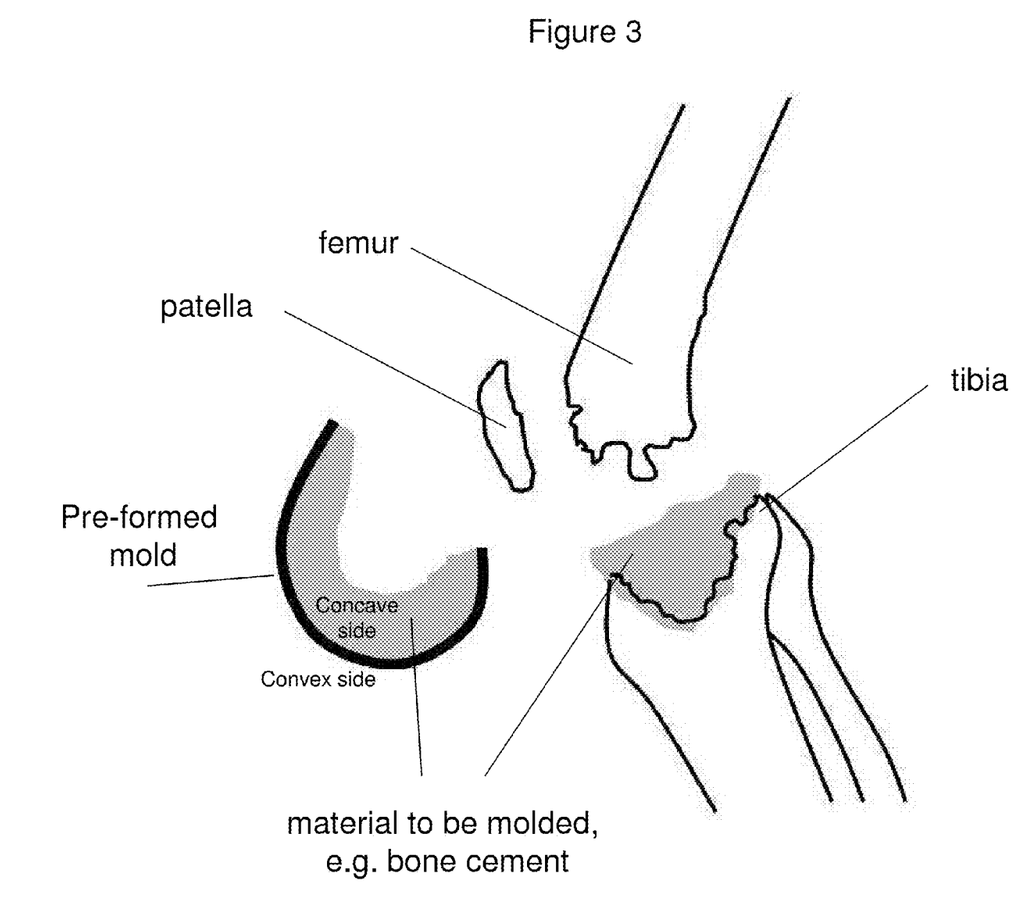
FIG. 3 demonstrates how, in accordance with an embodiment of the present invention, the material to be molded is placed on one side of the joint and within the concave side of the mold; in a particular embodiment of the present invention, the mold is made out of sheet metal and designed for molding bone cement, which has been mixed with at least one antibiotic. The material to be molded can be first placed on the tibia and then into the concave of the mold or vice versa. Apart from sheet metal, the mold can be made out of any other rigid material such as another metal or hard plastics or an elastic material such as silicone.
Figure 4:
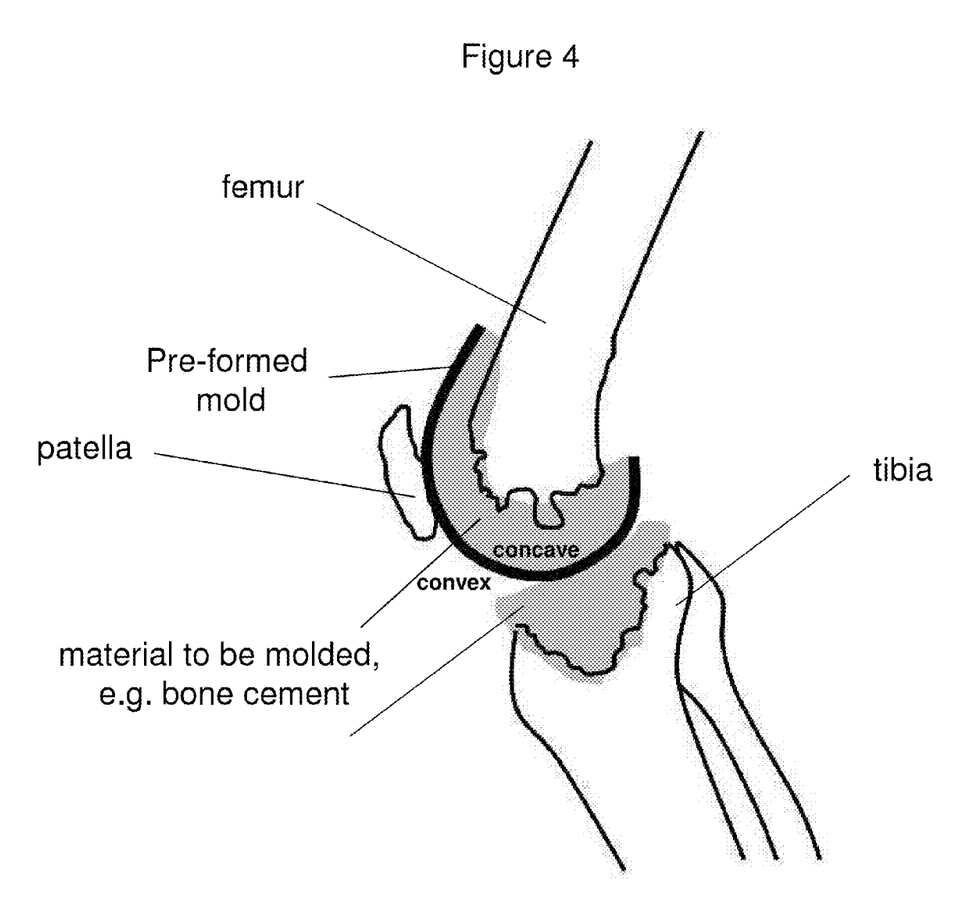
FIG. 4 demonstrates, in accordance with an embodiment of the present invention, how the mold of FIG. 3 is pressed onto the other side of the joint. The concave side of the mold forms one side of the newly formed joint surface and the convex side of the mold simultaneously forms the other side of the joint surface.
Figure 5:
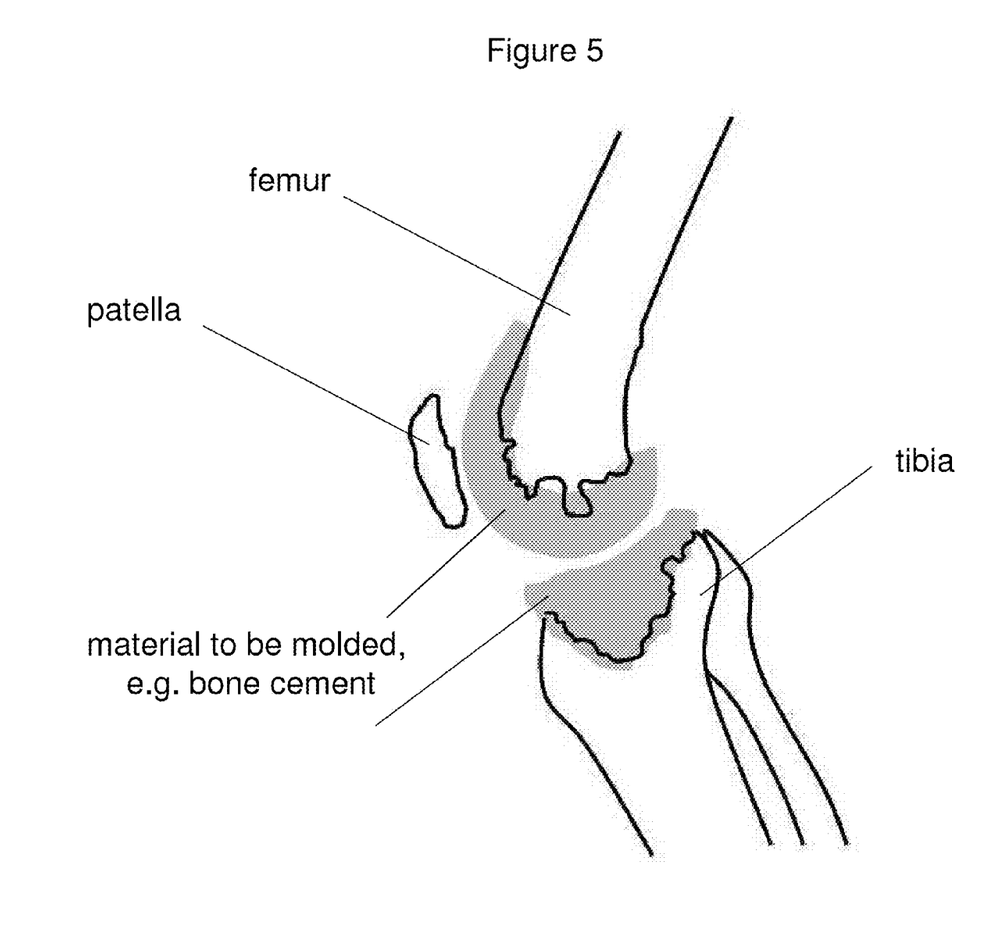
FIG. 5 illustrates, in accordance with an embodiment of the present invention, how the material has conformed to the irregular bone surface on each side of the joint, and, with removal of the mold, the material has been formed into mating parts at the new joint surface such that they can articulate with one another.

1. Provide a mold that is sized in accordance to the bony anatomy of the individual in need of arthoplasty. The mold can be made out of (i) a rigid material such as a metal, e.g. stainless steel sheet metal, or hard plastic or (ii) an elastic material such as silicone. The mold might be pretreated to facilitate easy detachment of the filling material from the mold or the mold can be manufactured from a rigid or elastic material that inherently facilitates easy detachment of the filling material from the mold. 2. Mix the bone cement or other biocompatible material with antibiotics to obtain a standard antibiotic concentration ('molding mixture') 3. Before the molding mixture hardens, take half of the molding mixture and coat the concave side of the mold with it (FIG. 3). 4. Flex the knee and press the mold filled with molding mixture onto the end of the distal femur. 5. Take the remaining molding mixture and place it on the tibial surface (FIG. 3). The material to be molded can be first placed on the tibia and then into the concave of the mold and onto the end of the distal femur or vice versa. 6. Extend the knee, holding the leg in proper alignment while the molding mixture totally hardens (FIG. 4). The mold acts on both the tibial and femoral surfaces, and creates conforming surfaces compatible with motion of the joint. 7. Once the molding mixture has hardened, flex the knee again and remove the mold. The material has conformed to the irregular bone surface on each side of the joint, thus achieving a custom fit, and the material has been formed into mating parts at the new joint surface that can articulate with one another (FIG. 5). 8. Now one has an articulating spacing device that is custom made for the resected bone surface(s).

Example 2

Process for Creating an Articulating Spacing Device Using a Sheet-Metal Mold and Bone Cement-Antibiotics Mixture Following the surgical preparation (see above under materials), the orthopaedic surgeon creates a bone cement-antibiotics mixture ('cement') by mixing bone cement with antibiotics such as tobramycin (3.6 grams per 40 gram package of bone cement) or vancomycin (3.0 grams per 40 gram package of bone cement).

Figure 7:
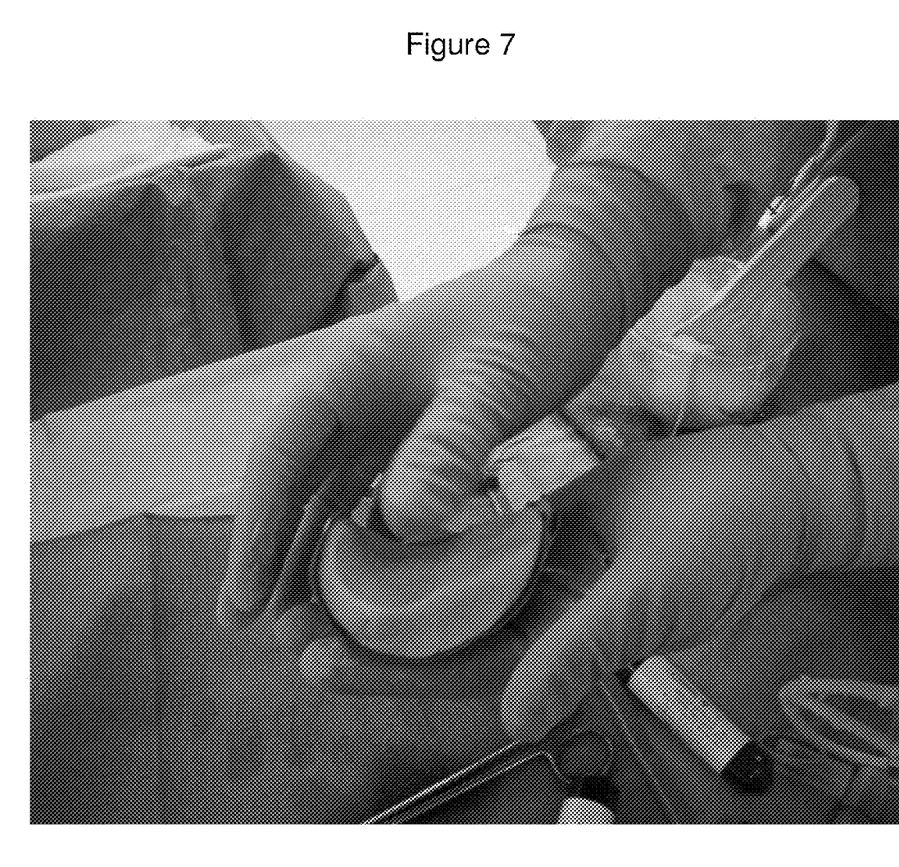
FIG. 7 shows, in accordance with an embodiment of the present invention, a stainless sheet-metal mold whose concave side is being filled with a molding bone cement-antibiotic mixture.
Figure 8:
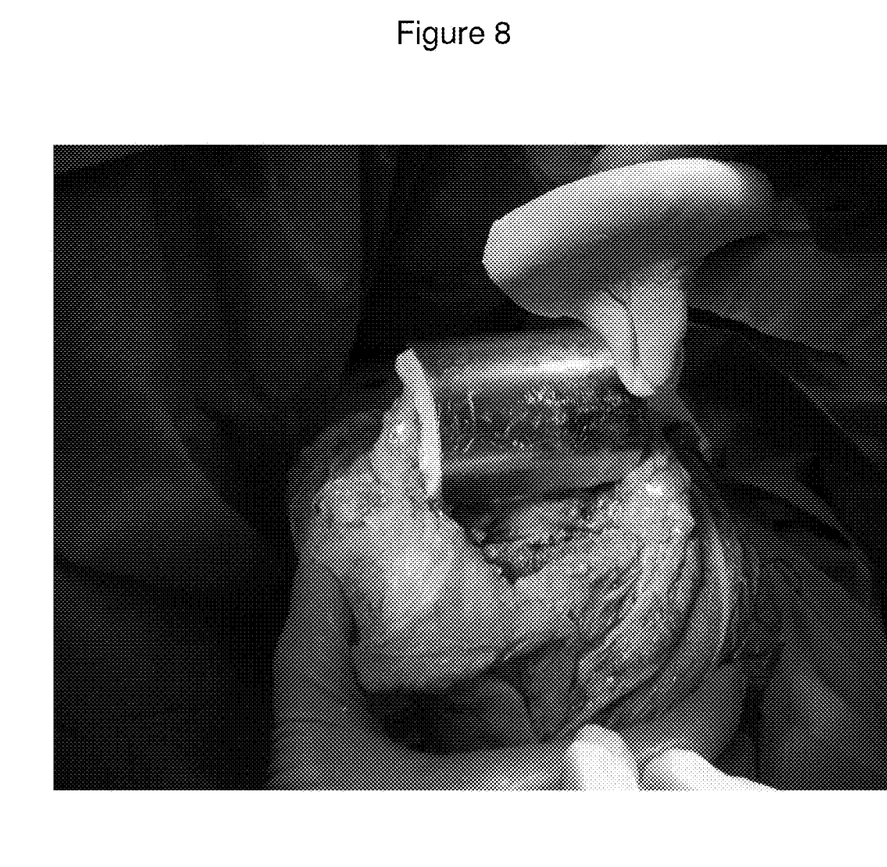
FIG. 8 shows, in accordance with an embodiment of the present invention, a bone cement-filled sheet-metal mold that has been applied onto the distal femur.
Figure 9:
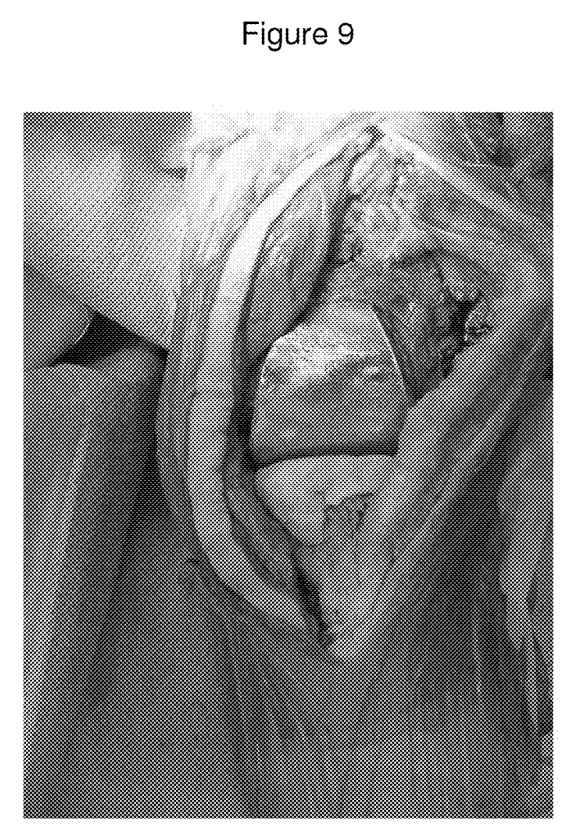
FIG. 9 shows, in accordance with an embodiment of the present invention, a bone cement-filled sheet-metal mold that has been applied onto the distal femur, where, in addition, pliable cement has been applied to the tibia, while the knee has been maintained in an extended position. The sheet-metal mold is acting to simultaneously mold the cement on both the femoral and tibial sides of the joint.
Figure 10:
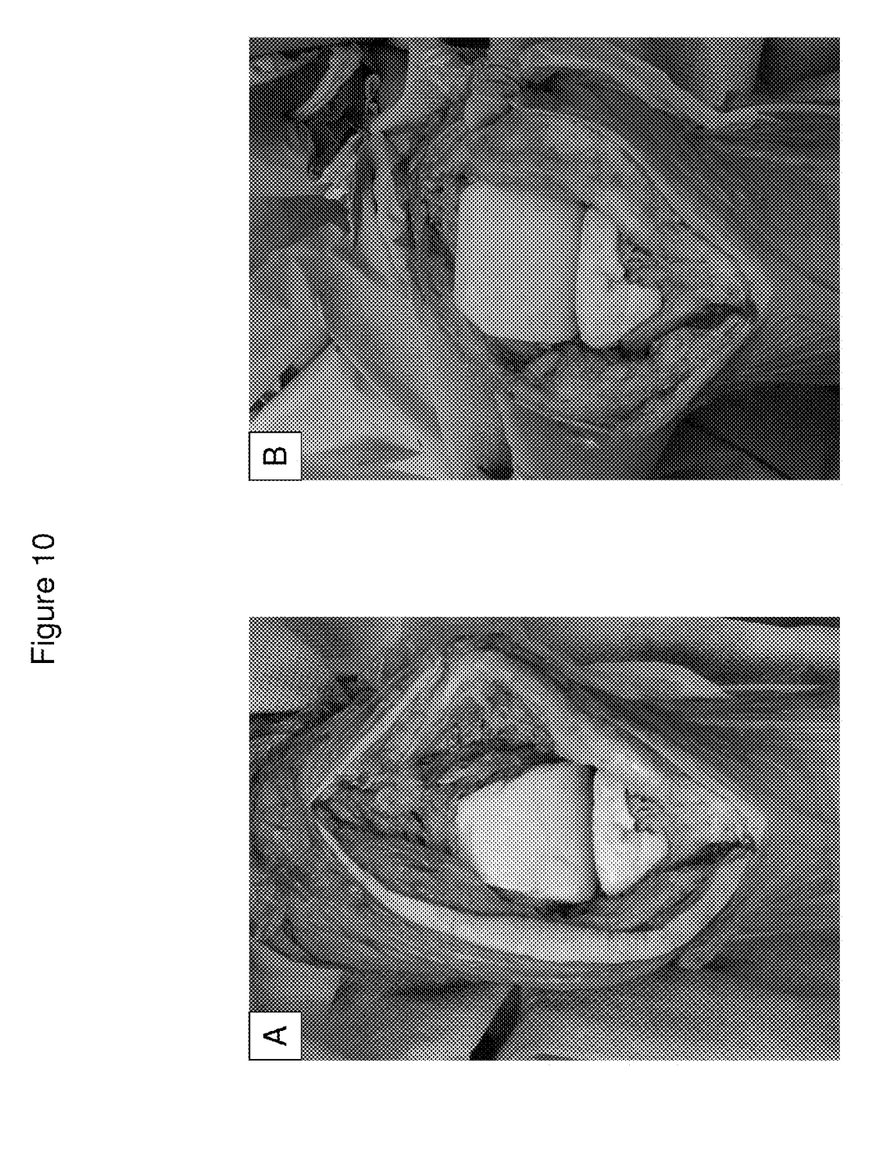
FIG. 10 shows, in accordance with an embodiment of the present invention, an articulating spacing device created out of molding bone cement. The spacing device ('spacer') exhibits two mating surfaces that allow for knee extension (PanelA) and knee flexion (Panel B).
Figure 11:
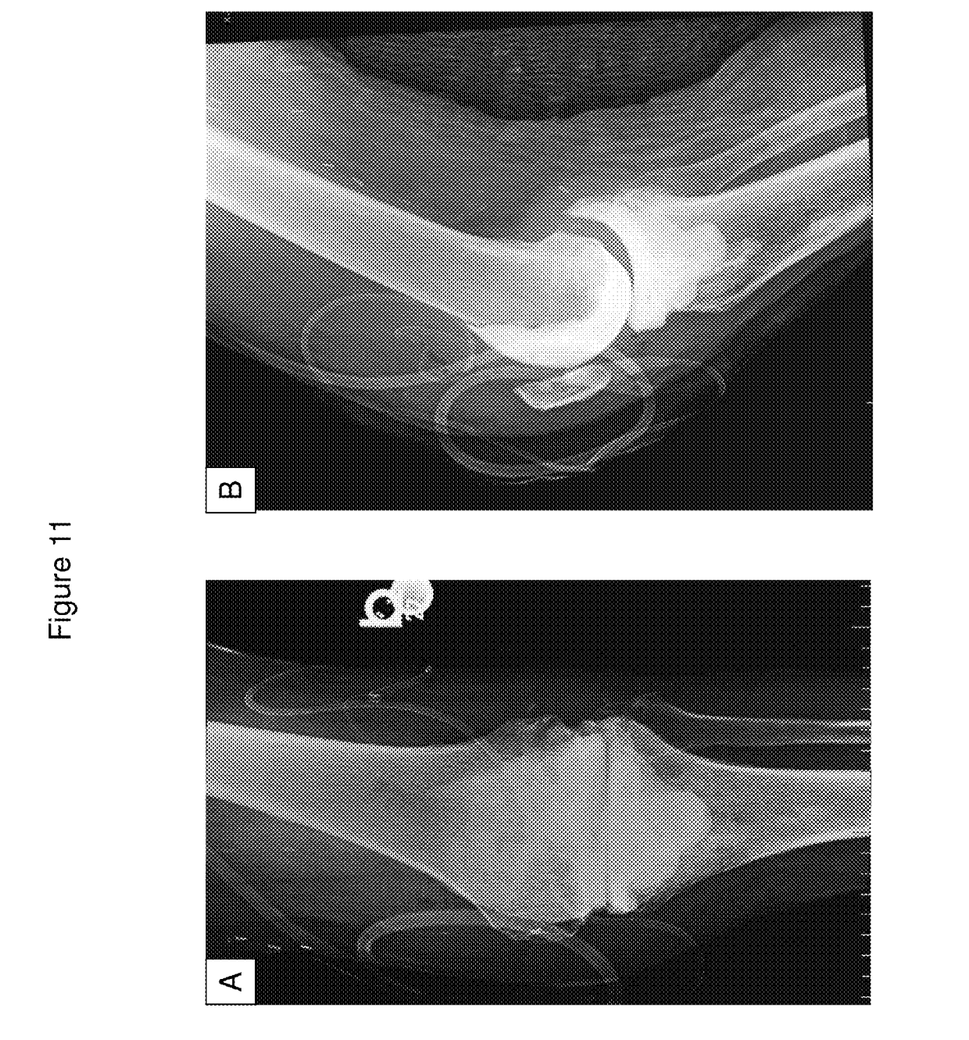
FIG. 11 shows postoperative x-rays of a patient with an articulating spacing device made out of bone cement, in accordance with an embodiment of the present invention. PanelA shows a frontal view and Panel B shows a lateral view.
Figure 12:
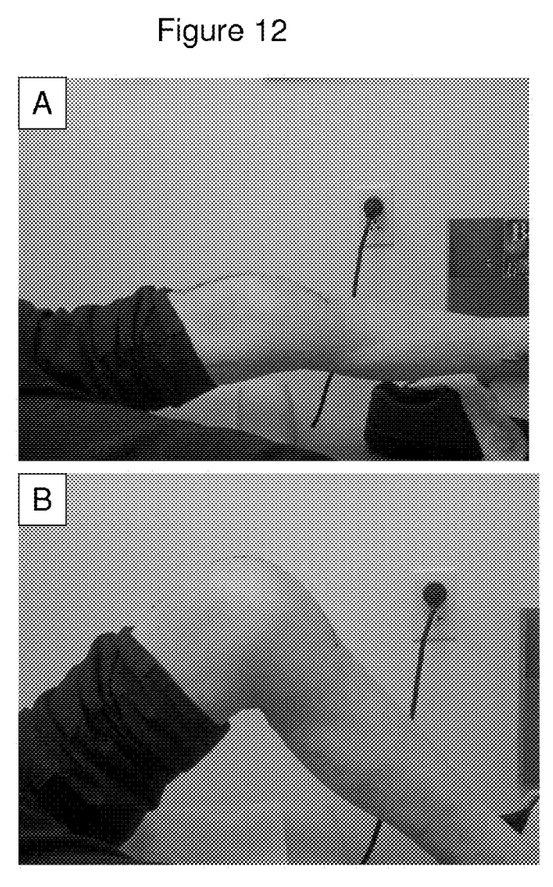
FIG. 12 shows a typical example of range of motion two weeks following implantation of an articulating spacing device, in accordance with an embodiment of the present invention. Panel A illustrates an extended position, while Panel B illustrates a flexed position.

Both sides of the sheet-metal mold are coated with mineral oil (FIGS. 6A and 6B) to facilitate later on easy detachment of the cement from the mold. The knee is fully flexed. When the cement is in a doughy state, the cement is applied to the concave side of the mold (FIG. 7). The mold is then gently pressed onto the distal femur (FIG. 8) and excess cement from around the mold is removed. Care is directed towards minimizing the amount of excess cement in the mold and the pressurization of cement into the bone of the femur to allow for ease of later extraction. Care is also directed towards maintaining the proper level of the joint line. Additional cement, which is still doughy, is then applied to the tibia. The knee is then extended and held in the desired full extension with 6 degrees of valgus (FIG. 9). The convex side of the mold forms the cement on the tibia into a shape that mates with the femoral side of the mold. The cement on both sides of the joint is then allowed to harden, while the leg is held in the proper position. When the cement is hard, the knee is flexed again and the mold is easily removed. One then has an articulating cement spacing device for the knee with two mating surfaces that allow for knee flexion and extension (FIGS. 10A and 10B). The wound is then closed over the articulating cement spacer. Only antibiotic cement is left in the knee. There is no retained metal or polyethylene. Depending on the quality of the tissue overlying the knee and the type of exposure performed, the patient may be allowed to begin range of motion exercises of the knee right after surgery. Postoperative x-rays are shown of a patient who received a spacing device, as described (FIG. 11A frontal view and 11B lateral view). An example of range of motion at the two week time point when the patient returned for suture removal is shown (FIG. 12A extended position and 12B flexed position).

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Hofmann A A, Goldberg T, Tanner A M and Kurtin S M (2005). Treatment of infected total knee arthroplasty using an articulating spacer.
*Clinical Orthopaedics & Related Research* 430, pp. 125-131.
Whiteside L A (1994). Treatment of infected total knee arthroplasty.
*Clinical Orthopaedics & Related Research* 299, pp. 169-172.
Wilde A H & Ruth J T (1988). Two-Stage Reimplantation in Infected Total Knee Arthroplasty.
*Clinical Orthopaedics & Related Research* 236, pp. 23-35.

What is claimed is:

1. A method of forming one-piece articulating spacing device for a patient's knee joint, the method comprising the steps of
    (1) providing a rigid one-piece mold, said mold comprising:
    a main body portion comprising a concave and a convex surface, wherein said body portion is shaped to allow controlled movement of said joint;
    a cavity defined by said concave and convex surfaces for receiving biocompatible material;
    wherein said mold is configured for being located, in situ, between the patient's distal femoral bone and proximal tibial bone;
    wherein said mold is dimensioned for custom forming said biocompatible material to optimally fit to said patient's femoral and tibial bones; and
    wherein said mold is configured to form in situ an articulating surface simultaneously for articulation of the femoral surface with the corresponding tibial surface.
    (2) placing a suitable amount of pliable biocompatible material within said cavity;
    (3) contacting said patient's femoral bone with said biocompatible material within the concave surface of said mold;
    (4) with the mold on the femoral bone still in place, adding pliable biocompatible material to said patient's tibial bone in such way that the resulting shape mates with the convex surface of said mold;
    (5) letting said biocompatible material within said cavity of said mold and on said tibial bone harden;
    (6) removing said mold.
2. The method of claim 1, wherein said biocompatible material is mixed with at least one antibiotic suitable for release from said biocompatible material.
3. The method of claim 1, wherein said articulating spacing device is a permanent spacing device for the knee.
4. The method of claim 1, wherein said articulating spacing device is a temporary spacing device for the knee.

* * * * *